Figure 1:
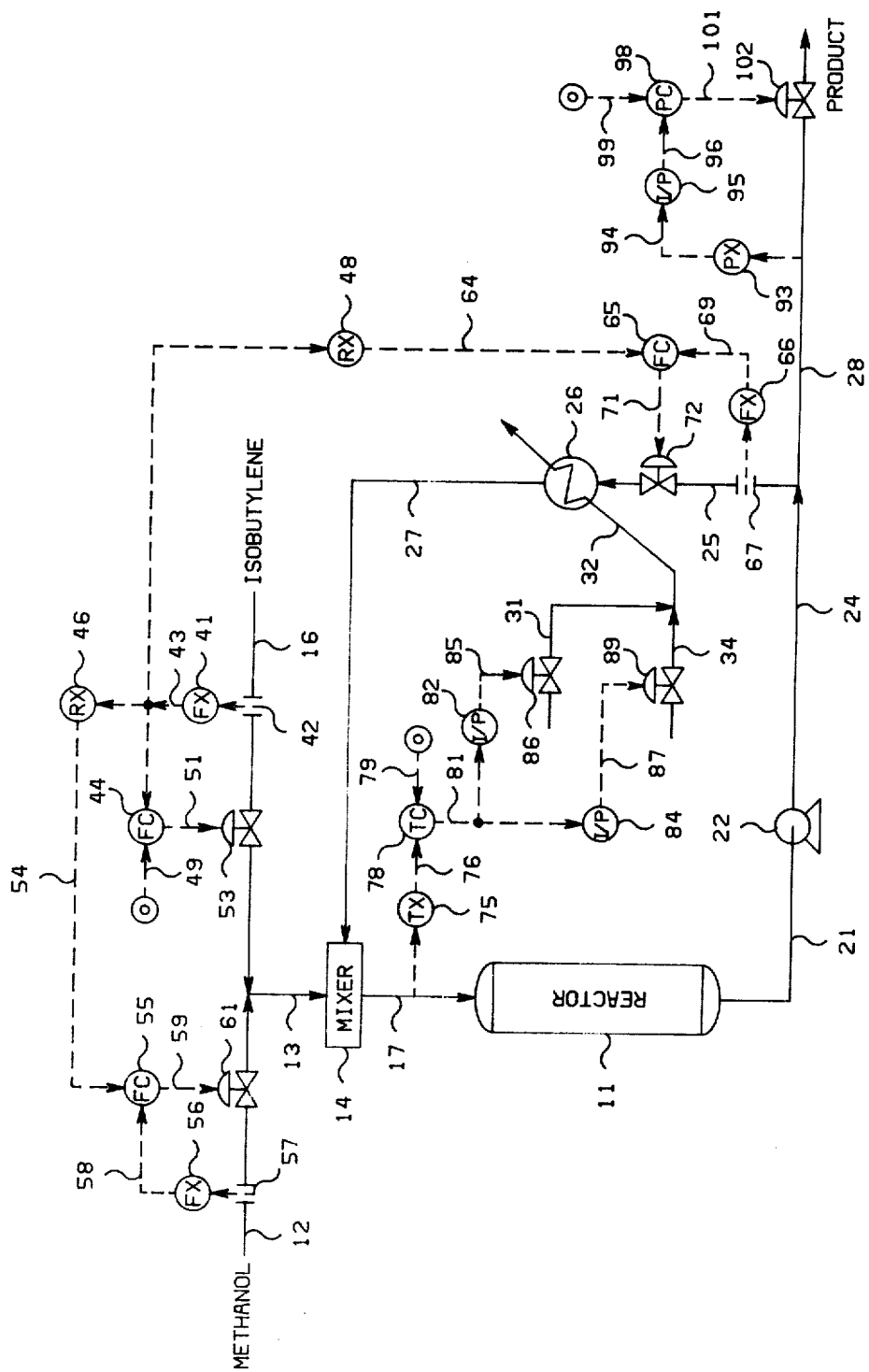

United States Patent [19]

Makovec

[11] 4,290,110
[45] Sep. 15, 1981

[54] TEMPERATURE CONTROL FOR A REACTOR

[75] Inventor: Donald J. Makovec, Bartlesville, Okla.

[73] Assignee: Phillips Petroleum Co., Bartlesville, Okla.

[21] Appl. No.: 92,779

[22] Filed: Nov. 8, 1979

[51] Int. Cl.³ .......................... G06G 7/58; G05D 11/13
[52] U.S. Cl. ................................ 364/500; 23/230 A; 364/109; 422/111
[58] Field of Search ............... 364/500, 501, 502, 109; 23/230 A; 422/108, 109, 110, 111, 62; 585/263

[56] References Cited

U.S. PATENT DOCUMENTS

| | | | |
|---|---|---|---|
| 2,977,288 | 3/1961 | Cabbage | 196/132 |
| 3,002,818 | 10/1961 | Berger | 364/500 X |
| 3,497,449 | 2/1970 | Urban | 364/500 X |
| 3,619,377 | 11/1971 | Palmer et al. | 364/501 X |
| 3,748,448 | 7/1973 | Sayles et al. | 364/500 |
| 3,958,943 | 5/1976 | Carmassi et al. | 364/501 X |
| 3,979,461 | 9/1976 | Ancillotti | 585/864 X |
| 4,069,413 | 1/1978 | Rutledge et al. | 364/118 |
| 4,115,862 | 9/1978 | Stewart | 364/500 |
| 4,166,770 | 9/1979 | Anderson et al. | 364/501 X |

Primary Examiner—Joseph F. Ruggiero

[57] ABSTRACT

Control of the temperature rise across a reactor where a portion of the product stream flowing from the reactor is recycled and mixed with the feed flowing to the reactor is accomplished by controlling the flow rate of the recycle stream to thus control the concentration of the reactants flowing to the reactor in such a manner that a desired temperature differential across the reactor is obtained. The inlet temperature to the reactor is controlled by manipulating the temperature of the recycle stream to thus maintain the inlet temperature to the reactor at some desired temperature. Ratio control is utilized to maintain a desired ratio of reactants flowing to the reactor if more than one reactant is flowing to the reactor.

9 Claims, 1 Drawing Figure

TEMPERATURE CONTROL FOR A REACTOR

This invention relates to control of a chemical reactor where a portion of the product stream flowing from the reactor is recycled and mixed with the feed flowing to the reactor. In one aspect this invention relates to method and apparatus for controlling the temperature rise across a reactor where a portion of the product stream flowing from the reactor is recycled and mixed with the feed flowing to the reactor. In another aspect this invention relates to method and apparatus for controlling the inlet temperature of a reactor where a portion of the product stream flowing from the reactor is recycled and mixed with the feed flowing to the reactor. In still another aspect this invention relates to method and apparatus for controlling the ratio of at least two reactants flowing to a reactor, if more than one reactant is flowing to the reactor, where a portion of the product stream flowing from the reactor is recycled and mixed with the feed flowing to the reactor.

Reactors where a portion of the product stream flowing from the reactor is recycled and mixed with the feed flowing to the reactor are utilized in many chemical processes. In order to obtain a desired percent conversion of the reactants to the desired product, it is often necessary to control both the inlet temperture of the reactor and the temperature rise across the reactor. Close control of the temperature rise across the reactor is also required for safety purposes.

It is thus an object of this invention to provide method and apparatus for controlling the temperature rise across a reactor where a portion of the product stream flowing from the reactor is recycled and mixed with the feed flowing to the reactor. It is another object of this invention to provide method and apparatus for controlling the inlet temperature of a reactor where a portion of the product stream flowing from the reactor is recycled and mixed with the feed flowing to the reactor.

In many chemical processes employing a reactor where a portion of the product stream flowing from the reactor is recycled and mixed with the feed flowing to the reactor, at least two reactants are mixed prior to introduction into the reactor. Close control of the ratio of the reactants is necessary to insure that the desired product is obtained and to avoid wasting reactants.

It is thus another object of this invention to provide method and apparatus for controlling the ratio of at least two reactants flowing to a reactor, if more than one reactant is flowing to the reactor, where a portion of the product stream flowing from the reactor is recycled and mixed with the feed flowing to the reactor.

In accordance with the present invention, method and apparatus is provided whereby the flow rate of at least one reactant flowing to a reactor, where a portion of the product stream flowing from the reactor is recycled and mixed with the feed flowing to the reactor, is measured. This measured flow rate is utilized to establish a set point for the flow rate of the recycle stream to the reactor. In this manner, a desired concentration of at least one reactant is maintained in the feed flowing to the reactor thus insuring a desired temperature rise across the reactor.

Control of the inlet temperature of the reactor is accomplished by measuring the inlet temperature of the reactor and controlling the temperature of the recycle stream in response to the measured inlet temperature to thereby maintain the inlet temperature of the reactor at a desired temperature. Ratio control of the reactants, if more than one reactant is flowing to the reactor, is accomplished by measuring the flow rate of one of the reactants and utilizing this measured flow rate to derive set points for the flow rate of the remaining reactants.

Other objects and advantages of the invention will be apparent from the foregoing brief description of the invention and the claims as well as the detailed description of the drawing in which:

FIG. 1 is a diagrammatic illustration of a reactor, where a portion of the product stream flowing from the reactor is recycled and mixed with the feed flowing to the reactor, and an associated control system.

The invention is illustrated and described in terms of a process for manufacturing methyl t-butyl ether. The invention, however, is applicable to other manufacturing processes where it is desirable to control the temperature rise across a reactor and the inlet temperature to the reactor as well as the ratio of the reactants flowing to the reactor.

Essentially only two reactants, methanol and isobutylene, are required to produce methyl t-butyl ether. However, the ratio control of the reactants is applicable to more than two reactants. The temperature control of the present invention is applicable to reactors to which only one reactant is supplied even though the description is in terms of two reactants supplied to a reactor.

Although the invention is illustrated and described in terms of a specific reactor configuration and a specific control system for the reactor, the invention is also applicable to different types and configurations of reactors where a portion of the product stream flowing from the reactor is recycled and mixed with the feed flowing to the reactor as well as different types of control system configurations which accomplish the purpose of the invention. Lines designated as signal lines in the drawings are electrical or pneumatic in this preferred embodiment. However, the invention is also applicable to mechanical, hydraulic or other signal means for transmitting information. In almost all control systems some combination of these types of signals will be used. However, use of any other type of signal transmission, compatible with the process and equipment in use is within the scope of the invention.

The controllers shown may utilize the various modes of control such as proportional, proportional-integral, proportional-derivative, or proportional-integral-derivative. In this preferred embodiment, proportional-integral controllers are utilized but any controller capable of accepting two input signals and producing a scaled output signal, representative of a comparison of the two input signals, is within the scope of the invention. The operation of proportional-integral controllers is well known in the art. The output control signal of a proportional-integral controller may be represented as $$S = K_1 E + K_2 \int E \, dt$$

where
 S = output control signals;
 E = difference between two input signals; and
 $K_1$ and $K_2$ = constants.

The scaling of an output signal by a controller is well known in control systems art. Essentially, the output of a controller may be scaled to represent any desired factor or variable. An example of this is where a desired pressure and an actual pressure is compared by a controller. The output could be a signal representative of a desired change in the flow rate of some gas necessary to make the desired and actual pressures equal. On the other hand, the same output signal could be scaled to represent a percentage or could be scaled to represent a temperature change required to make the desired and actual pressures equal. If the controller output can range from 3 to 15 pounds, which is typical, then the output signal could be scaled so that an output signal having a pressure of 9 pounds corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more of such equipment types. While the presently preferred embodiment of the invention preferably utilizes a combination of pneumatic control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. In addition, all signals could be translated into a "suppressed zero" or other similar format in order to provide a "live zero" and prevent an equipment failure from being erroneously interpreted as a "low" or "high" measurement or control signal. Regardless of the signal format or the exact relationship of the signal to the parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to FIG. 1, a methyl t-butyl ether reactor 11 is illustrated. Any desired type of reactor may be utilized although a fixed catalyst bed reactor is presently preferred. Any suitable catalyst may be utilized in the reactor 11. Amberlyst 15 which is an ion exchange resin obtainable from Rohm and Haas is a preferred catalyst. Methanol is provided through a combination of conduit means 12 and 13 to the mixer 14. Isobutylene is provided through the combination of conduit means 16 and 13 to the mixer 14. Typically, the isobutylene will be provided in the $C_4$ stream from a catalytic cracker. The $C_4$ stream from a catalytic cracker will generally contain in the range of about 10 to about 30 percent isobutylene. The reactants are combined in conduit means 13 and are mixed in the mixer 14. The thus mixed reactants are provided through conduit means 17 to the reactor 11.

The reaction product is withdrawn from the reactor 11 through conduit means 21. A portion of the reaction products flows from the pumping means 22 through the combination of conduit means 24 and 25 to the heat exchanger 26. From the heat exchanger 26, the reaction products flowing through conduit means 25 are provided through conduit means 27 to the mixer 24. The reaction products flowing through conduit means 27 are typically referred to as the recycle stream.

The portion of the reactor products which are not recycled are removed as a product stream through conduit means 28. A portion of the product stream will typically be methyl t-butyl ether.

A heating fluid is provided to the heat exchanger 26 through the combination of conduit means 31 and 32. A cooling fluid is provided to the heat exchanger 26 through the combination of conduit means 34 and 32. Typically, during startup of the reactor, heat must be supplied to the recycle stream. After the reaction has reached steady state, typically a cooling fluid will be required to cool the recycle stream to thereby maintain a desired inlet temperature to the reactor 11.

The process described to this point is a typical process for manufacturing methyl t-butyl ether. It is the manner in which the process for manufacturing methyl t-butyl ether is controlled to maintain a desired temperature rise across the reactor 11, maintain a desired inlet temperature to the reactor 11, and maintain a desired ratio of the reactants flowing to the reactor 11 which presents the novel features of the present invention.

Flow transducer 41 in combination with flow sensor 42, which is operably located in conduit means 16, establishes a signal 43 which is representative of the flow rate of the feed flowing through conduit means 16. Signal 43 is provided from the flow transducer 41 to the flow controller 44, the ratio transducer 46, and the ratio transducer 48.

The flow controller 44 is also provided with a set point signal 49 which is representative of the desired flow rate of the feed flowing through conduit means 16. In response to signals 43 and 49, the flow controller 44 establishes an output signal 51 which is responsive to the difference between signals 43 and 49. Signal 51 is provided from the flow controller 44 to the pneumatic control valve 53 which is operably located in conduit means 16. The pneumatic control valve 53 is manipulated in response to signal 51 to thereby maintain the flow rate of the feed flowing through conduit means 16 substantially equal to the desired flow rate represented by the set point signal 49.

In response to signal 43, the ratio transducer 46 establishes an output signal 54 which is representative of the flow rate of the methanol flowing through conduit means 12 which is required to maintain a desired ratio of the methanol to the isobutylene. Typically, the desired ratio of methanol to isobutylene will range from about 1:1 to about 1.2:1. Signal 54 is provided from the ratio transducer 46 to the flow controller 55.

Flow transducer 56 in combination with flow sensor 57, which is operably located in conduit means 12, establishes an output signal 58 which is representative of the flow rate of the feed flowing through conduit means 12. Signal 58 is provided as the second input to the flow controller 55. In response to signals 54 and 58, the flow controller 55 establishes an output signal 59 which is responsive to the differences between signals 54 and 58. Signal 59 is provided from the flow controller 55 to the pneumatic control valve 61 which is operably located in conduit means 12. The pneumatic control valve 61 is manipulated in response to signal 59 to thereby maintain the flow rate of the feed flowing through conduit means 12 substantially equal to the desired flow rate represented by signal 54. In this manner, the ratio of the methanol to the isobutylene flowing to the reactor 11 is maintained at a desired ratio.

The inlet temperature to reactor 11 is preferably maintained at a temperature of about 130° F. The temperature rise across the reactor 11 is preferably limited to about 20° F. An inlet temperature of about 130° F. would thus result in an outlet temperature of about 150° F. which would typically provide an isobutylene of about 92 weight percent.

The preferred flow rate of the feed flowing through conduit means 13 to the mixer 14 is about 5 volumes of feed/volumes of catalyst/hour. Typically, at this preferred flow rate, the flow rate of the recycle stream flowing through conduit means 27 should be about 15 volumes of recycle feed/volume of catalyst/hour or about 3 volumes of recycle stream per volume of feed flowing through conduit means 13. This dilution will typically limit the temperature rise across the reactor 11 to about 20° F. when the feed stream flowing through conduit means 16 contains about 15 volume percent isobutylene which is typical.

The manner in which the temperature rise across the reactor and the inlet temperature to the reactor is controlled is as follows. In response to signal 43, the ratio transducer 48 establishes an output signal 64 which is representative of the flow rate of the recycle stream flowing through conduit means 25 required to dilute the reactants flowing to the reactor 11 sufficiently to limit the temperature rise across the reactor 11 to about 20° F. Signal 64 is provided from the ratio transducer 48 as an input to the flow controller 65.

Flow transducer 66 in combination with flow sensor 67, which is operably located in conduit means 25, establishes an output signal 69 which is representative of the flow rate of the recycle stream flowing through conduit means 25. Signal 69 is provided from the flow transducer 66 as a second input to the flow controller 65. In response to signal 64 and 69, the flow controller 65 establishes an output signal 71 which is responsive to the difference between signals 64 and 69. Signal 71 is provided from the flow controller 65 to the pneumatic control valve 72 which is operably located in conduit means 25. The pneumatic control valve 72 is manipulated in response to signal 71 to thereby maintain the flow rate of the recycle stream flowing through conduit means 25 substantially equal to the flow rate represented by signal 64. In this manner, the temperature rise across the reactor 11 is effectively controlled.

Temperature transducer 75 in combination with a temperature sensing device such as a thermocouple which is operably located in conduit means 17 establishes an output signal 76 which is representative of the inlet temperature of the reactor 11. Signal 76 is provided as a first input to the temperature controller 78. The temperature controller 78 is also provided with a set point signal 79 which is representative of the desired inlet temperature of the reactor 11. Signal 79 is preferably set at about 130° F.

In response to signals 76 and 79, the temperature controller 78 establishes an output signal 81 which is responsive to the difference between signals 76 and 79. Signal 81 is provided from the temperature controller 78 to the current to pressure (I/P) transducer 82 and is also provided to the I/P transducer 84. Signal 81 is converted from electrical form to a pneumatic form by the I/P transducer 82 and is provided as signal 85 to the pneumatic control valve 86 which is operably located in conduit means 31. The pneumatic control valve 86 is manipulated in response to signal 85 to thereby maintain a desired flow rate of the heating fluid flowing through conduit means 31. In like manner, signal 81 is converted from electrical form to pneumatic form by the I/P transducer 84 and is provided as signal 87 to the pneumatic control valve 89 which is operably located in conduit means 34. The pneumatic control valve 89 is manipulated in response to signal 87 to thereby maintain a desired flow rate of the cooling fluid flowing through conduit means 34.

Typically, the heating fluid flowing through conduit means 31 and the cooling fluid flowing through conduit means 34 will not be mixed. Thus, split range control is utilized to insure that only one of the pneumatic control valves 86 and 89 will be open at any one time. Preferably, the pneumatic control valve 86 will be fully open when signal 85 has a value of 3 pounds and will be fully closed when signal 85 has a value of 9 pounds or more. Pneumatic control valve 89 will be fully closed when signal 87 has a value of 9 pounds or less and will be fully open when signal 87 has a value of 15 pounds. If the inlet temperature of the reactor is at the set point, signal 81 will remain constant. If the inlet temperature of the reactor moves from the set point, the value of signal 81 will change to produce a change in the flow rate of either the heating fluid or the cooling fluid provided to the heat exchanger 26 to maintain the inlet temperature to the reactor substantially equal to the set point represented by signal 79. In this manner, effective temperature control of the inlet temperature of the reactor is accomplished.

The production of methyl t-butyl ether is preferably carried out at a pressure in the range of about 100 psi to about 200 psi. The desired reaction pressure for the reaction is maintained by pressure control on the flow rate of the product stream flowing through conduit means 28. Pressure transducer 93 in combination with a pressure sensing device, which is operably located in conduit means 28, establishes an output signal 94 which is representative of the pressure of the product stream flowing through conduit means 28 and is thus representative of the system pressure for the methyl t-butyl ether process. Signal 94 is provided from the pressure transducer 93 to the I/P converter 95. Signal 94 is converted from electrical form to pneumatic form and is provided as signal 96 to the pressure controller 98. The pressure controller 98 is also provided with a set point signal 99 which is representative of the desired system pressure for the methyl t-butyl ether process. Signal 99 will typically have a value in the range of about 100 psi to about 200 psi as has been previously stated. In response to signals 96 and 99, the pressure controller 98 establishes an output signal 101 which is responsive to the difference between signals 96 and 99. Signal 101 is provided as an input to the pneumatic control valve 102 which is operably located in conduit means 28. The pneumatic control valve 102 is manipulated in response to signal 101 to thus maintain a desired system operating pressure for the methyl t-butyl ether process.

The invention has been described in terms of a presently preferred embodiment as is illustrated in FIG. 1. Specific components which can be used in the practice of the invention as illustrated in FIG. 1 such as flow sensors 57, 42, and 67; flow transducers 56, 41 and 66; flow controllers 55, 44, and 65; ratio transducers 46 and 48; pneumatic control valves 61, 53, 86, 89, 72 and 102; temperature transducer 75; temperature controller 78; pressure transducer 93; pressure controller 98; and I/P transducers 82, 84 and 95 are each well known, commerically available control components such as are described at length in Perry's Chemical Engineers Handbook, 4th Edition, Chapter 22, McGraw Hill.

For reasons of brevity, conventional auxilliary equipment such as additional pumps, additional heat exchangers, additional measurement-control devices, etc. have not been included in the above description as they play no part in the explanation of the invention.

While the invention has been described in terms of the presently preferred embodiment, reasonable variations and modifications are possible by those skilled in the art, within the scope of the described invention and the appended claims. Variations such as utilizing the control system on a chemical process other than the methyl t-butyl ether process, using more than one reactor, or supplying the heating and cooling fluids to separate heat exchangers is within the scope of the present invention.

That which is claimed is:

1. Apparatus comprising:
   a reactor;
   means for supplying a first feed stream containing a first reactant to the feed inlet of said reactor;
   means for withdrawing the reaction product from said reactor;
   means for passing a portion of said reaction product as a recycle stream to the feed inlet of said reactor;
   means for establishing a first signal representative of the flow rate of said first feed stream;
   means, responsive to said first signal, for establishing a second signal representative of the flow rate of the recycle stream required to substantially maintain a desired temperature differential across said reactor;
   means for establishing a third signal representative of the actual flow rate of said recycle stream;
   means for comparing said second signal and said third signal and for establishing a fourth signal responsive to the difference between said second signal and said third signal; and
   means for manipulating the flow rate of said recycle stream in response to said fourth signal to thereby maintain a desired temperature differential across said reactor.

2. Apparatus in accordance with claim 1 wherein said means for establishing said second signal comprises a ratio transducer.

3. Apparatus in accordance with claim 1 additionally comprising:
   means for establishing a fifth signal representative of the actual feed inlet temperature of said reactor;
   means for establishing a sixth signal representative of the desired feed inlet temperature of said reactor;
   means for comparing said fifth signal and said sixth signal and for establishing a seventh signal responsive to the difference between said fifth signal and said sixth signal; and
   means for manipulating the temperature of said recycle stream in response to said seventh signal to thereby maintain a desired feed inlet temperature for said reactor.

4. Apparatus in accordance with claim 3 additionally comprising:
   means for supplying a second feed stream containing a second reactant to the feed inlet of said reactor;
   means for establishing an eighth signal representative of the desired flow rate of said first feed stream;
   means for comparing said first signal and said eighth signal and for establishing a ninth signal responsive to the difference between said first signal and said eighth signal;
   means for manipulating the flow rate of said first feed stream in response to said ninth signal to thereby maintain the flow rate of said first feed stream substantially equal to the desired flow rate represented by said eighth signal;
   means for establishing a tenth signal representative of the flow rate of said second feed stream required to maintain a desired ratio of said second reactant to said first reactant in response to said first signal;
   means for establishing an eleventh signal representative of the actual flow rate of said second feed stream;
   means for comparing said tenth signal and said eleventh signal and for establishing a twelfth signal responsive to the difference between said tenth signal and said eleventh signal; and
   means for manipulating the flow rate of said second feed stream in response to said twelfth signal to thereby maintain a desired ratio of said second reactant to said first reactant in said reactor.

5. A method for controlling the temperature differential across a reaction zone, where a portion of the product stream flowing from said reaction zone is passed as a recycle stream and mixed with the feed stream flowing to said reaction zone before said feed stream is introduced into said reaction zone, wherein said feed stream contains a first reactant, said method comprising the steps of:
   establishing a first signal representative of the flow rate of said feed stream before said feed stream is mixed with said recycle stream;
   establishing a second signal representative of the flow rate of said recycle stream required to substantially maintain a desired temperature differential across said reaction zone in response to said first signal;
   establishing a third signal representative of the actual flow rate of said recycle stream;
   comparing said second signal and said third signal and establishing a fourth signal responsive to the difference between said second signal and said third signal; and
   manipulating the flow rate of said recycle stream in response to said fourth signal to thereby maintain a desired temperature differential across said reaction zone.

6. A method in accordance with claim 5 additionally comprising the steps of:
   establishing a fifth signal representative of the actual inlet temperature of said reaction zone;
   establishing a sixth signal representative of the desired inlet temperature of said reaction zone;

comparing said fifth signal and said sixth signal and establishing a seventh signal responsive to the difference between said fifth signal and said sixth signal; and manipulating the temperature of said recycle stream in response to said seventh signal to thereby maintain a desired feed inlet temperature for said reaction zone.

7. A method for controlling the temperature differential across a reaction zone where a portion of the product stream flowing from said reaction zone is passed as a recycle stream and mixed with the reaction zone feed stream, which is formed from at least a first feed stream containing a first reactant and a second feed stream containing a second reactant, before said reaction zone feed stream is introduced into said reaction zone, said method comprising the steps of:

establishing a first signal representative of the flow rate of said first feed stream;

establishing a second signal representative of the flow rate of said recycle stream required to substantially maintain a desired temperature differential across said reaction zone in response to said first signal;

establishing a third signal representative of the actual flow rate of said recycle stream;

comparing said second signal and said third signal and establishing a fourth signal responsive to the difference between said second signal and said third signal; and manipulating the flow rate of said recycle stream in response to said fourth signal to thereby maintain a desired temperature differential across said reaction zone.

8. A method in accordance with claim 7 additionally comprising the steps of:

establishing a fifth signal representative of the actual feed inlet temperature of said reaction zone;

establishing a sixth signal representative of the desired feed inlet temperature of said reaction zone;

comparing said fifth signal and said sixth signal and establishing a seventh signal responsive to the difference between said fifth signal and said sixth signal; and manipulating the temperature of said recycle stream in response to said seventh signal to thereby maintain a desired feed inlet temperature for said reaction zone.

9. A method in accordance with claim 8 additionally comprising the steps of:

establishing an eighth signal representative of the desired flow rate of said first feed stream;

comparing said first signal and said eighth signal and establishing a ninth signal responsive to the difference between said first signal and said eighth signal;

manipulating the flow rate of said first feed stream in response to said ninth signal to thereby maintain the flow rate of said first feed stream substantially equal to the desired flow rate represented by said eighth signal;

establishing a tenth signal representative of the flow rate of said second feed stream required to maintain a desired ratio of said second reactant to said first reactant in response to said first signal;

establishing an eleventh signal representative of the actual flow rate of said second feed stream;

comparing said tenth signal and said eleventh signal and establishing a twelfth signal responsive to the difference between said tenth signal and said eleventh signal; and manipulating the flow rate of said second feed stream in response to said twelfth signal to thereby maintain a desired ratio of said second reactant to said first reactant in said reaction zone.

* * * * *